United States Patent [19]
Pitelka et al.

[11] Patent Number: 5,494,087
[45] Date of Patent: Feb. 27, 1996

[54] APPARATUS FOR AIDING IN THE PREPARATION OF AN INJECTION SERUM

[76] Inventors: Karen J. Pitelka, 7817 Whiterim Terr., Potomac, Md. 20854; Laddie Pitelka, 51 Offshore, Hilton Head, S.C. 29928

[21] Appl. No.: 322,126

[22] Filed: Oct. 13, 1994

[51] Int. Cl.[6] .................................................. B65B 3/04
[52] U.S. Cl. .................................. 141/375; 141/1; 141/2; 141/27; 141/273; 141/319; 141/329; 141/378; 604/411; 604/414; 211/74; 211/77; 211/81; 211/164; 248/311.3
[58] Field of Search ................................. 141/21, 25–27, 141/271, 273, 319, 329, 330, 375–378, 1, 2, 18, 320–322, 130; 604/407, 411, 414; 211/70, 71, 74, 77, 78, 81, 164; 248/311.2, 311.3

[56] References Cited

U.S. PATENT DOCUMENTS

| | | | |
|---|---|---|---|
| 1,736,392 | 11/1929 | Coss et al. | |
| 2,064,815 | 12/1936 | Armstrong | 141/375 X |
| 2,122,722 | 7/1938 | O'Neill | 604/414 |
| 2,677,372 | 5/1954 | Barnish | 604/414 |
| 2,687,838 | 8/1954 | Wallingford et al. | 141/329 X |
| 2,861,570 | 11/1958 | Beecher | 604/407 |
| 3,230,986 | 1/1966 | Worley | 141/375 |
| 3,661,189 | 5/1972 | Bowser et al. | 141/1 |
| 3,734,147 | 5/1973 | Borutta et al. | 141/27 |
| 3,807,464 | 4/1974 | Pitesky | 141/375 X |
| 3,840,011 | 10/1974 | Wright | 604/407 |
| 3,853,158 | 12/1974 | Whitty | 141/27 |
| 3,875,979 | 4/1975 | Hults | 141/27 |
| 4,278,225 | 7/1981 | Phelps | 248/311.3 |
| 4,316,558 | 2/1982 | Kubiak | 222/181 |
| 4,434,820 | 3/1984 | Glass | 141/2 |
| 4,489,766 | 12/1984 | Montada | 141/27 |
| 5,012,845 | 5/1991 | Averette | 141/329 |
| 5,037,390 | 8/1991 | Raines et al. | 211/74 X |
| 5,167,928 | 12/1992 | Kelly et al. | 422/99 |
| 5,247,972 | 9/1993 | Tetreault | 141/27 |
| 5,309,959 | 5/1994 | Shaw et al. | 141/130 |
| 5,431,201 | 7/1995 | Torchia et al. | 141/329 X |

FOREIGN PATENT DOCUMENTS 2939110  4/1981  Germany ................................ 604/414

*Primary Examiner*—J. Casimer Jacyna
*Attorney, Agent, or Firm*—Morgan & Finnegan

[57] ABSTRACT

An apparatus for aiding in the preparation of an injectable serum is provided which comprises a two-part assembly including a stabilizing base and a framed support. The apparatus includes a support arm for receiving one or more conventional medicine vials which is rotatable about a horizontal axis. The apparatus further includes a support arm for receiving one or more conventional syringes which is disposed horizontally and in substantially parallel relationship with respect to the vial receiving support arm. This arrangement facilitates accurate alignment of syringes and vials which are being utilized in the preparation of the injection serum.

9 Claims, 3 Drawing Sheets

APPARATUS FOR AIDING IN THE PREPARATION OF AN INJECTION SERUM

FIELD OF THE INVENTION

The present invention relates to an apparatus for aiding in the preparation of an injection serum and more particularly pertains to an apparatus adapted to facilitate the preparation of an injectable medicament wherein the preparation operation requires the use of multiple syringes and/or multiple medicine vials.

DESCRIPTION OF THE PRIOR ART

Many patients who are on a daily self-injection regime either have impaired eyesight or lack the dexterity required to accurately perform the syringe filling operation. The use of syringe filling devices has therefore been contemplated by the prior art. More specifically, syringe filling devices heretofore devised and utilized for the purpose of assisting a user in filling a syringe with a desired quantity of medicine which is extracted from a sealed vial are known to consist basically of familiar, expected, and obvious structural configurations. These types of devices are designed primarily for patients who are required to give themselves regular injections at home over an extended period of time.

By way of example, the prior art discloses in U.S. Pat. No. 2,677,372, to Barish, Jr., U.S. Pat. No. 3,875,979, to Hults, U.S. Pat. No. 4,489,766, to Montada, and U.S. Pat. No. 3,853,158 to Whitty devices which include means for supporting a vial such that its contents may be withdrawn by a syringe.

However, many patients who must self-administer drugs at home often times must actually prepare the serum which must be injected. This is accomplished by extracting a specific quantity of a diluent from a sterile vial into a syringe. The extracted quantity in the syringe is then injected into a second vial which contains a powdered or concentrated form of a medication which must be mixed with the diluent, thus forming the drug to be administered. The secondary dilution operation requires the user to perforate the central portion of the rubber seal of the vial with the needle of a syringe and evacuate the previously extracted quantity of diluent into the vial. This operation has proven to be difficult for many persons who are afflicted with poor eyesight or suffering from spasticity in their hands.

The injection dose aids of the prior art are only adapted to assist a user with the initial extraction operation. If a person's treatment requires the secondary dilution in order to prepare the injection serum, the user must physically remove the filled syringe from the dosing aid and perform the dilution operation without the assistance of the device.

Therefore, it can be appreciated that there exists a continuing need for an improved injection dosing apparatus which can be used for aiding a user in both filling a syringe with a quantity of liquid medication or diluent from a first vial and subsequently evacuating that quantity of liquid from the syringe into a second vial. In this regard, the present invention substantially fulfills this need.

In this respect, the injection dosing apparatus according to the present invention substantially departs from the conventional concepts and designs of the prior art, and in doing so provides an apparatus primarily developed for the purpose of facilitating both the extraction and the dilution operations which are required in the preparation of an injection serum for self-administration.

SUMMARY OF THE INVENTION

The general object of the present invention, which will be described subsequently in greater detail, is to provide an improved apparatus for aiding in the preparation of an injectable serum and a method associated therewith.

In particular, it is an object of the present invention to provide an apparatus adapted to facilitate the preparation of an injectable medicament wherein the preparation operation requires the use of multiple syringes and/or multiple medicine vials.

It is a further object of the present invention to provide an apparatus which is capable of facilitating both filling a syringe with liquid which is withdrawn from a sealed vial and also transferring liquid contained within a syringe into a sealed vial.

It is another object of the present invention to provide an apparatus which can be utilized by persons who are on a medical treatment regime which requires self-administration of injections.

It is a further object of the present invention to provide an apparatus which allows persons suffering from poor eyesight or an affliction which causes hand tremors or shakiness to easily and accurately prepare and administer injections at home without any assistance from medical personnel.

An even further object of the present invention is to provide an apparatus which would be beneficial in assisting a person in filling a syringe with medication wherein the medication being administered is either in a premixed form or in a form which requires a subsequent mixing operation.

Even still another object of the present invention is to provide an apparatus for aiding in the preparation and administration of an injection serum wherein the preparation thereof requires the use of multiple syringes and medicine vials.

Accomplishing these and other objects, the present invention provides an apparatus for aiding in the preparation of an injectable serum which comprises a two-part assembly including a stabilizing base and a framed support. The apparatus includes a means for receiving one or more conventional medicine vials, which is rotatable about a horizontal axis. The apparatus further includes a means for receiving one or more conventional syringes which is disposed horizontally and in substantially parallel relationship with respect to the vial receiving means. This arrangement facilitates accurate alignment of the syringes and vials when liquid is being transferred from a vial to a syringe.

If a treatment regimen requires a subsequent mixing operation before injection, a patient may have to transfer the liquid which has been filled in the syringe into a second vial which contains a powdered or concentrated form of a medication. In order to aid in the transfer of liquid from a syringe to a vial, the stabilizing base is provided with a plurality of wells which are formed in the outer surface of the base. The second vial may be placed within one of the wells in the base which will hold the vial steady while the needle of the previously filled syringe is inserted. The liquid may then be easily ejected into the second vial to form the injection serum.

Therefore, various combinations of syringe to vial or vial to syringe operations are possible to accomplish using the apparatus of the present invention, thus making the apparatus of the present invention adaptable to different treatment regimens.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description of a preferred embodiment thereof. Such description makes reference to the annexed drawings wherein.

The same reference numerals refer to the same parts through the various Figures.

DESCRIPTION OF THE PREFERRED EMBODIMENT

Figure 1:
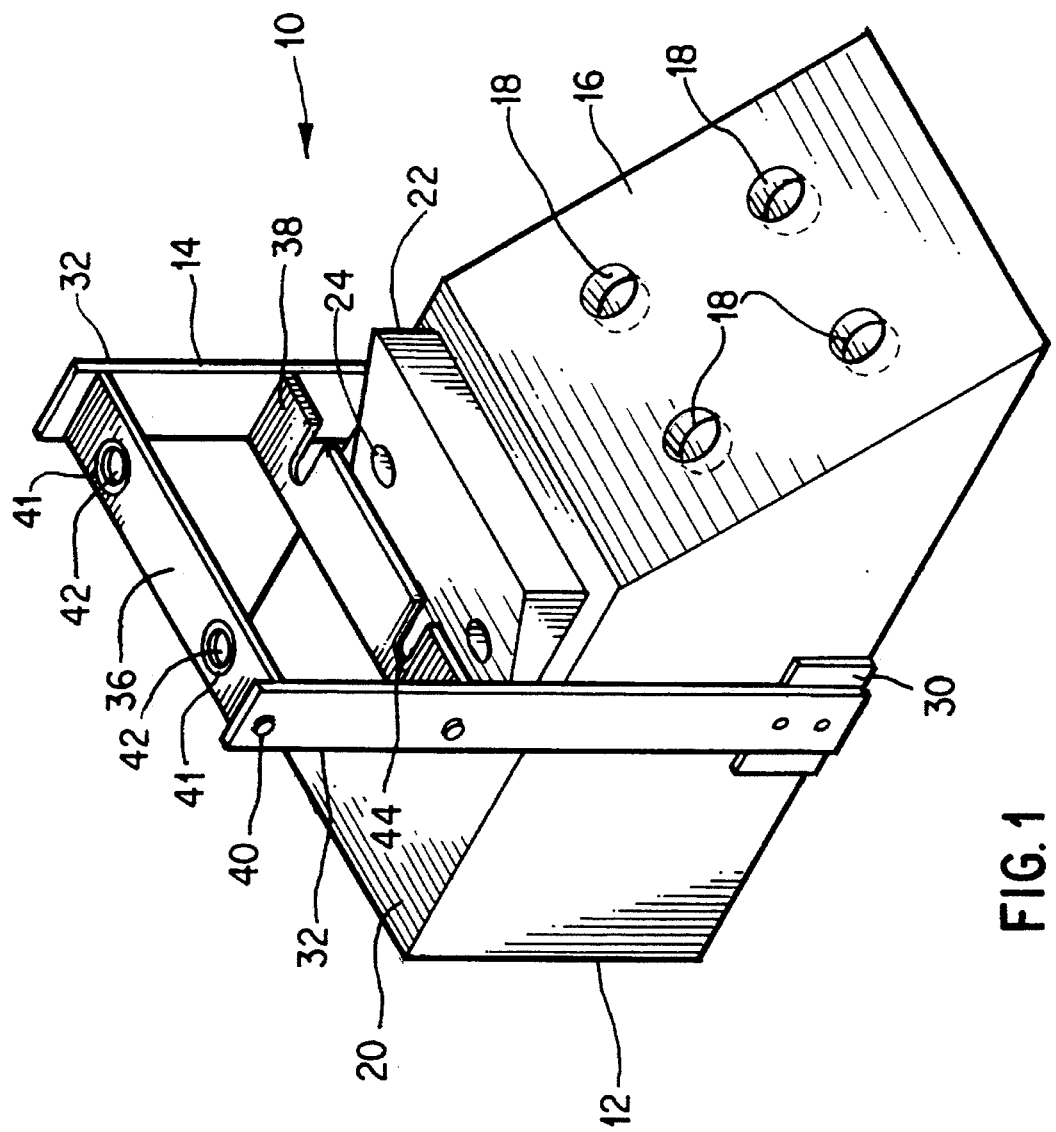
FIG. 1 is a perspective view of the preferred embodiment of the apparatus for aiding in the preparation of an injection serum constructed in accordance with the principles of the present invention.

With reference now to the drawings, and in particular to FIG. 1 thereof, the preferred embodiment of the apparatus embodying the principles and concepts of the present invention and generally designated by the reference numeral 10 will be described.

Figure 4:
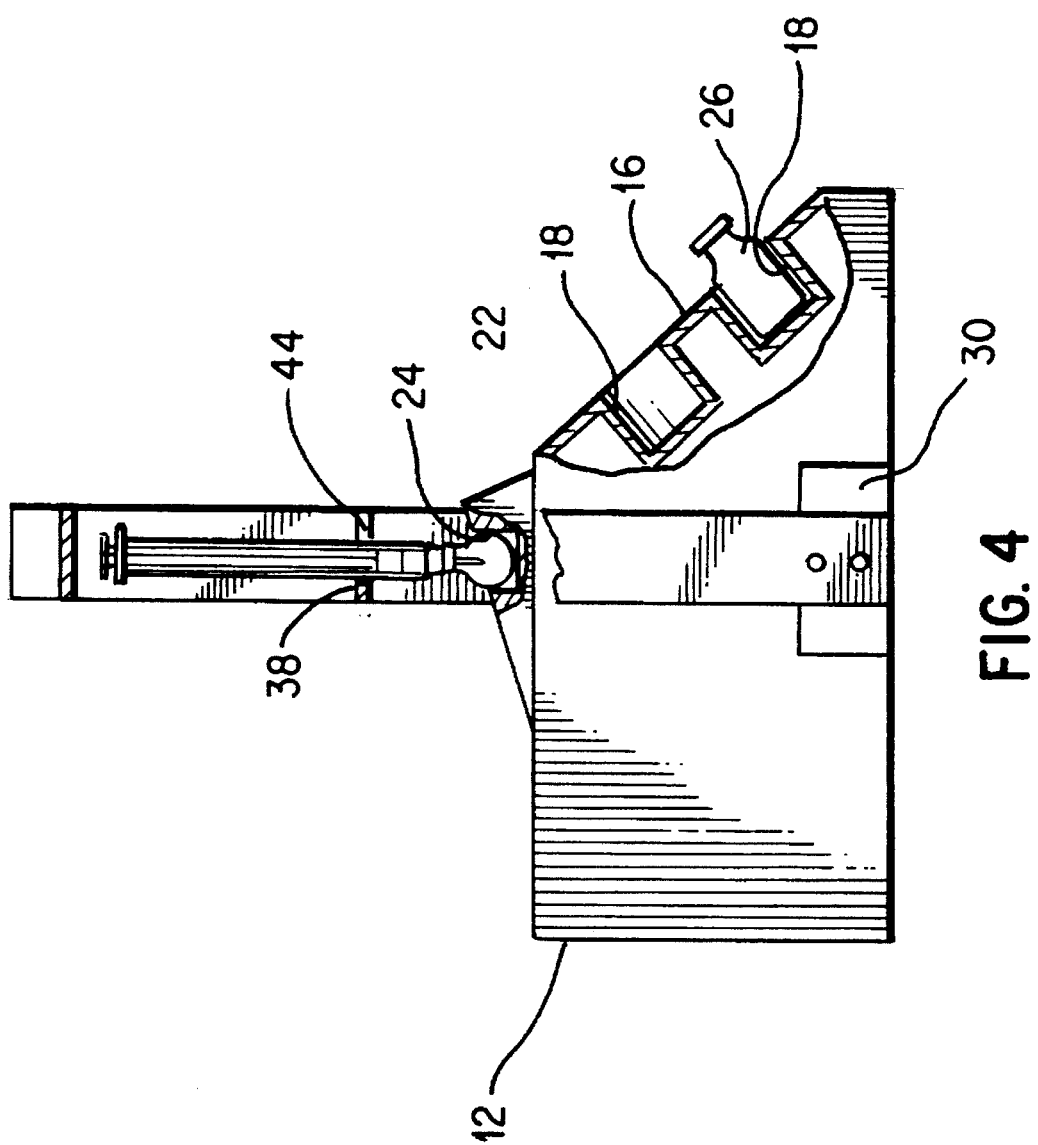
FIG. 4 is a side elevational view in taken in cross-section.

More specifically, it will be noted in the various Figures that there is shown an apparatus 10 for aiding in the preparation of an injectable serum. The apparatus 10 includes two independent components, a stabilizing base 12, and an upstanding frame member 14. Although each of the components 12,14 could function independently with respect to specific uses, in the preferred embodiment of the present invention, the base 12 and frame member 14 are utilized together. Thus, in the operative assembled configuration as shown in FIGS. 1 and 4, the stabilizing base 12 is positioned on a planar portion 34 of the platform 30 of the frame member 14.

The stabilizing base 12 is preferably of solid construction and formed of wood, metal, plastic or resin, or other suitable material. The stabilizing base 12 is generally rectangular in shape, thus having six exterior faces. Each of the exterior faces is consistent with a rectangular prism with the exception that one face 16, instead of being oriented perpendicularly with respect to its adjacent faces is angled outwardly at approximately a 45° angle so as to form a sloped surface 16.

The sloped surface 16 is provided with multiple wells 18 formed thereon. The first wells 18 are adapted so as to accommodate the receipt of a conventional medicine vial 26 therein.

The upper surface 20 of the stabilizing base has attached thereto a sloped triangular projection 22. The projection may be either integrally formed with the base 12 or may be fabricated separately and attached to the base 12 by an adhesive, a mechanical fastener, or any conventional means.

The projection 22 is provided with at least one well 24 formed therein. The wells 24 are also sized so as to accommodate a conventional medicine vial 26. It is contemplated that due to the solid construction of the stabilizing base 12, when a vial 26 is placed within any of the wells 18,24 of the base 12, a person can easily insert the needle of a syringe 28 into the rubber seal portion of the vial 26. When utilizing the base 12 as a stabilizer for the vial 26, the needle placement operation may be accomplished using only one hand. Therefore, a person suffering from a physical affliction which causes reduced dexterity will be considerably aided in that when placing a needle into a vial 26, the person can concentrate on accurately puncturing the sealed portion of the vial 26 without worrying about holding the vial 26 steady.

It is additionally contemplated that by the design of the present invention, the stabilizing base 12 may be used for holding vials either for storage or when evacuating a liquid medication or diluent from a syringe 28 into a vial 26 which contains a powdered or concentrated form of a medication in order to form a serum to be injected.

Figure 3:
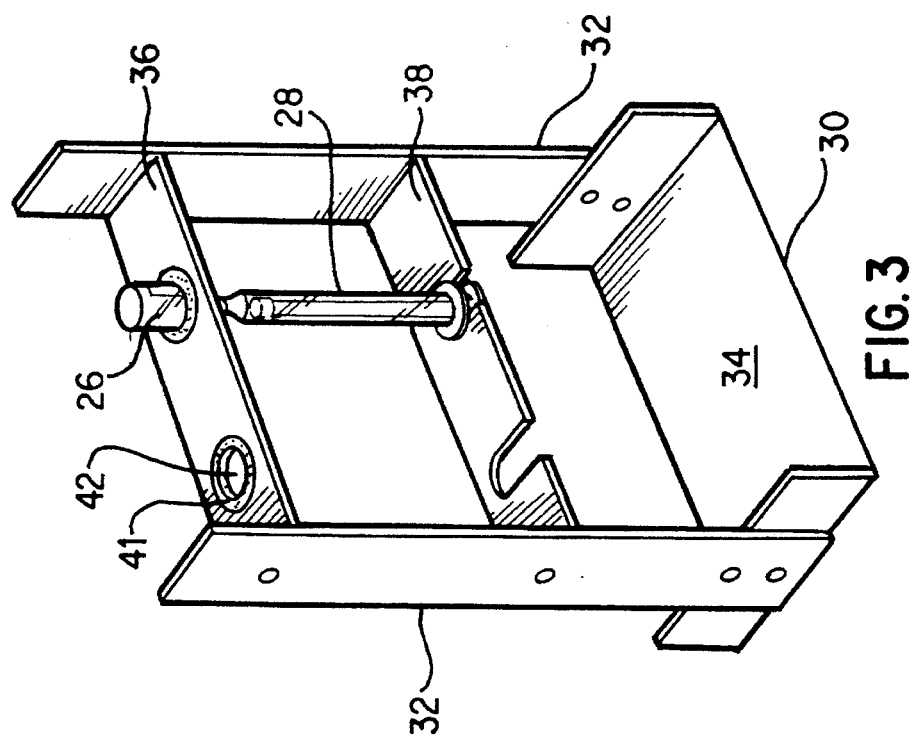
FIG. 3 is a perspective view of the support section after the vial has been inverted to allow its contents to be transferred into the syringe.
Figure 2:
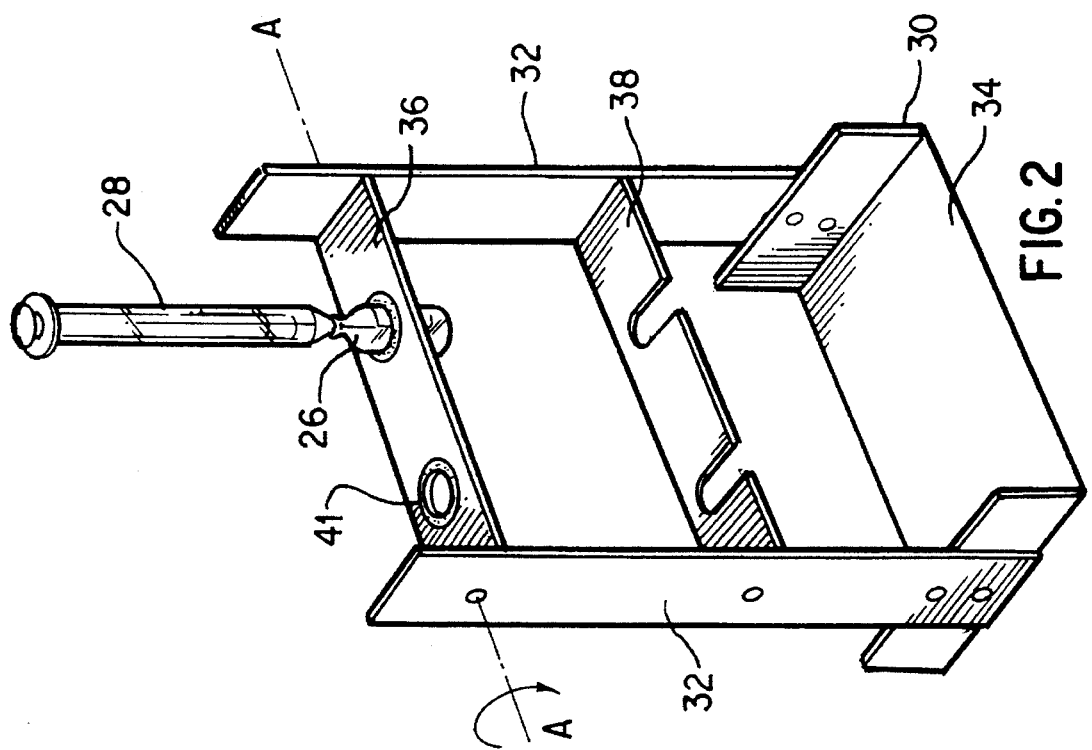
FIG. 2 is a perspective view of the support section of the apparatus showing a vial and syringe housed therein.

To transfer liquid from a vial to a syringe, the design of the frame member 14 allows the vial 26 to be oriented at a level above that of the syringe 28 as shown in FIG. 3 so as to accomplish complete removal of the liquid contents from the vial 26. The frame member 14 in its preferred embodiment, is fabricated from metal but it is additionally contemplated that any material displaying sufficient rigidity, such as many plastics and resins, could be substituted for metal without departing from the invention.

The frame member 14 includes a U-shaped platform base 30. Two vertical upstanding arms 32 are attached in perpendicular orientation with respect to the planar portion 34 of the platform 30. The arms 32 are attached to the platform 30 by rivets, screws, or any other mechanical fastening design expedient.

In use, the stabilizing base 12 is positioned on the flat portion 34 of the platform 30 as shown in FIGS. 1 and 4. The interior dimensions of the frame member 14 are designed to be substantially identical to the exterior dimensions of the base 12. Therefore, when the frame member 14 and base 12 are in an assembled position, the base 12, being of solid construction, acts to stabilize the frame member 14 and ensure the frame member 14 is held steady and remains in vertical, upstanding orientation. In the preferred embodiment, the base 12 and frame member 14 do not include any separate fastening means but are held together merely due to the dimensional specifications set forth above so as to allow ease in assembly of the apparatus. However, it is contemplated that fasteners could be employed without departing from the spirit of the invention.

The frame member 14 further includes a vial support 36 and a syringe support 38. The vial and syringe supports 36,38 are disposed horizontally between the two upstanding arms 32 and parallel with respect to each other.

The syringe support 38 is fixedly attached to the upstanding arms 32 by rivets, screws, or other mechanical fastener. The vial support 36 is rotatably mounted about a horizontal axis A between the arms 32 and above the syringe support 38. The mounting mechanism 40 for the vial support 36 may include pins (not shown) which extend through each arm 32 and are seated within the vial support 36 at each distal end thereof. The length of the pin provides an axis of rotation to allow for rotational movement of the vial support 36. The mounting should include such frictional resistance so as to prevent uncontrolled movement of the support 36. Thus, the support 36 will not turn or rotate until force is applied by the user. The above described mounting mechanism 40 is merely illustrative and it is contemplated that the mounting mechanism could consist of any other known means which would impart the desired rotation to the vial support 36.

In order to accommodate one or more conventional medicine vials, the vial support 36 is provided with at least one aperture 42. Within the aperture 42, there is provided a bushing 41 formed of rubber or other such resilient material so that upon placement of the vial 26 therein, the vial will be held in frictional engagement therewith. The syringe support 38 is provided with at least one arcuate cut-out 44. Each of the cut-outs 44 is positioned in direct alignment with an aperture 42 of the vial support 36. The arcuate cut-out 44 is configured so as to allow the barrel portion of the syringe 28 to be removably inserted therein. The arcuate design allows for a clamping-like engagement of the barrel when it is introduced within the cut-out 44 and thus allows for ease in insertion and removal of the syringe within the confines of the cut-out 44.

The direct vertical or axial alignment between an aperture 42 and its complementary arcuate cut-out 44 provides for simultaneous engagement of both a vial 26 and a syringe 28 during a filling operation. When it is desired to fill a syringe with the liquid contents of a medicine vial, the vial 26 is placed within an aperture 42 of the vial support 36 and the needle of the syringe 28 is inserted within the rubber diaphragm seal (not shown) of the vial 26. With the syringe in place, the vial support 36 is rotated 180°, so as to invert both the vial 26 and syringe 28. At this point, the syringe 28 is juxtaposed adjacent to the aligned arcuate cut-out 44. The barrel of the syringe 28 is accordingly snapped within the cut-out 44 which will effectively hold the syringe 28 and the vial 26 in a fixed position. The plunger of the syringe may then be withdrawn so as to allow the liquid to flow downwardly from the vial 26 into the syringe 28. Therefore, it can be appreciated that the present invention is completely capable of aiding in dosing a single component medication such as insulin, which is purchased in a ready-to-use form.

The present invention is further adapted to accommodate and assist in the preparation of any type of injectable serum which requires two or more components to be mixed or diluted. The vial containing the first component is positioned within an aperture 42 of said vial support 36. The needle of the syringe 28 is then inserted within the rubber seal of the vial 26. The liquid is then extracted from the vial into the syringe in the same manner by rotating the vial support 36 as described above.

The second vial which may contain a powdered or concentrated form of a second component is then placed within one of the wells 24 of the base. The well 24 which is utilized will at that point in time be positioned directly below the now filled syringe. The filled syringe is then removed from the arcuate cut-out 44 and inverted 180 degrees so that the needle of the syringe is pointing downwardly toward the second vial. The needle of the syringe filled with the liquid obtained from the first vial is then inserted within the second vial which is being held in the well 24. The barrel of the syringe may be repositioned within the arcuate cut-out 44 so as to hold the syringe steady.

The plunger of the syringe is then slowly pushed downwardly to evacuate the liquid from the syringe into the second vial. The second vial is then agitated so as to adequately mix the two components to form an injectable serum of uniform consistency. It is contemplated that additional components could added or mixed as well using the same above described technique.

The second vial which contains the serum to be injected may then and probably is placed in an aperture 42 of the vial support 36 and the serum transferred to an injection syringe. The syringe containing the serum is then removed from the apparatus 10 and injected into a human body according to conventional techniques.

As to the manner of usage and operation of the present invention, the same should be apparent from the above description. Accordingly, no further discussion relating to the manner of usage and operation will be provided.

Once given the above disclosure may other features, modifications and improvements will become apparent to the skilled artisan. Such other features, modifications and improvements are therefore considered to be a part of this invention, the scope of which is to be determined by the following claims.

What is claimed is:

1. An apparatus for aiding in the preparation of an injectable serum comprising:

a stabilizing base and an upstanding frame member for receiving said base, said base having at least one well formed therein, said frame member including a pair of parallel support arms, one of said arms including at least one holding means for receiving a medical vial, and the other of said arms including at least one recess vertically aligned with said holding means;

said support arms overlying said stabilizing base when said base is associated with said frame with said recess being vertically aligned with said well, whereby a syringe may be supported by said recess when inserted into a medical vial located either in said holding means or said well.

2. The apparatus of claim 1, wherein said one arm is pivotable so that a syringe inserted into a vial located in said holding means from above may be inverted.

3. The apparatus of claim 1, wherein said pair of support arms includes an upper arm and a lower arm and wherein said at least one holding means comprises an aperture formed in said upper arm.

4. The apparatus of claim 3, wherein said at least one recess comprises an arcuate cut-out formed in said lower arm in substantial vertical alignment with said aperture.

5. The apparatus of claim 4, wherein said stabilizing base includes at least one side surface having at least one well formed therein.

6. The apparatus of claim 5, wherein said stabilizing base further includes an upper surface having at least one well in substantial vertical alignment with said aperture and said arcuate cut-out so as to enable multiple liquid transfer operations while preparing said injectable serum.

7. A method of using an apparatus for aiding in the preparation of an injectable serum comprising the steps of:

positioning a liquid containing vial on a pivotable support;

inserting a needle of a syringe into said vial from above;

rotating said support so as to invert said vial and said syringe and causing said syringe to fit in a recess in a second support;

withdrawing said liquid from said vial by syringe;

positioning a second vial in a support means below said second support;

removing said syringe;

repositioning said syringe in said recess in said second support;

discharging said liquid from said syringe into said second vial whereby said injectable serum is formed.

8. An apparatus for aiding in the preparation of an injectable serum comprising:
- a pair of vertically oriented, spaced apart support arms, each having a proximal end and a distal end;
- a first horizontal support arm fixedly disposed between the pair of vertical support arms and having at least one means for holding a syringe;
- a second horizontal support arm rotatably disposed between the pair of vertical support arms at a position vertically spaced from the first horizontal support arm, the second horizontal support arm having at least one means for holding a vial.

9. The apparatus of claim 8, further comprising:
- a stabilizing base having at least one well formed therein, said well being adapted for receiving a medical vial whereby said base may be positioned on said platform and between said pair of support arms.

* * * * *